(12) United States Patent
Yang et al.

(10) Patent No.: US 6,645,824 B1
(45) Date of Patent: Nov. 11, 2003

(54) COMBINED OPTICAL PROFILOMETRY AND PROJECTION MICROSCOPY OF INTEGRATED CIRCUIT STRUCTURES

(75) Inventors: Wenge Yang, Fremont, CA (US); Junwei Bao, Fremont, CA (US); Xinhui Niu, Los Altos, CA (US); Nickhil Jakatdar, Los Altos, CA (US); Yasuhiro Okumoto, Ibaraki (JP)

(73) Assignee: Timbre Technologies, Inc., Santa Clara, CA (US)

( * ) Notice: Subject to any disclaimer, the term of this patent is extended or adjusted under 35 U.S.C. 154(b) by 0 days.

(21) Appl. No.: 10/137,200

(22) Filed: Apr. 30, 2002

(51) Int. Cl.[7] .............................................. H01L 21/76
(52) U.S. Cl. ...................... 438/401; 438/401; 438/427; 438/753; 438/756; 73/1 J
(58) Field of Search ................. 438/401, 427, 438/753, 756; 73/1 J

(56) References Cited

U.S. PATENT DOCUMENTS 5,578,745 A * 11/1996 Bayer et al. ................. 73/1.73

* cited by examiner

*Primary Examiner*—David Nelms
*Assistant Examiner*—Mai-Huong Tran
(74) *Attorney, Agent, or Firm*—Morrison & Foerster LLP

(57) ABSTRACT

A metrology method and system of structures on a wafer includes obtaining a projection image of at least a first portion of the structures on the wafer using a first metrology apparatus. A profile of at least a second portion of the structure on the wafer is obtained using a second metrology apparatus. The information from the profile obtained using the second metrology apparatus and the information from the projection image obtained using the first metrology apparatus are combined using a processor.

33 Claims, 19 Drawing Sheets

| PROFILE TYPE | Binarization Method |
|---|---|
| 1. T-Top | Maximum/Minimum |
| 2. Footer | Fixed |
| 3. Hourglass | Maximum/Minimum |
| 4. Triangular | Fixed |
| 5. Square | Maximum/Minimum |
| 6. Convex Top | Inflection Point |
| 7. Concave Top | Fixed |

Density Value (lines / micron)

|  | 0.5 | 1.0 | 1.5 | 2.0 | 2.5 | 3.0 | 4.0 |
|---|---|---|---|---|---|---|---|
| 100 | 2 | 3 | 4 | 5 | 6 | 7 | 8 |
| 120 | 3 | 4 | 5 | 6 | 7 | 8 | 9 |
| 140 | 4 | 6 | 8 | 10 | 12 | 14 | ♦ |
| 160 | 5 | 7 | 9 | 11 | 13 | 15 | ♦ |
| 180 | 6 | 9 | 12 | 15 | 18 | ♦ | ♦ |
| 200 | 7 | 10 | 13 | 16 | ♦ | ♦ | ♦ |
| 220 | 8 | 11 | 14 | 17 | ♦ | ♦ | ♦ |

CD Value (nanometers) ← 2607

Density Value (lines / micron)

|  | 0.5 | 1.0 | 1.5 | 2.0 | 2.5 | 3.0 | 4.0 |
|---|---|---|---|---|---|---|---|
| 100 | -3 | -2 | -1 | 0 | 1 | 2 | 3 |
| 120 | -4 | -3 | -2 | -1 | 0 | 1 | 2 |
| 140 | 0 | 2 | 4 | 7 | 8 | 10 | ♦ |
| 160 | -1 | 1 | -1 | 0 | 1 | -1 | ♦ |
| 180 | 4 | 6 | 8 | 10 | 12 | ♦ | ♦ |
| 200 | 5 | 8 | 11 | 14 | ♦ | ♦ | ♦ |
| 220 | 6 | 10 | 15 | 25 | ♦ | ♦ | ♦ |

CD Value (nanometers) — 2608

COMBINED OPTICAL PROFILOMETRY AND PROJECTION MICROSCOPY OF INTEGRATED CIRCUIT STRUCTURES

CROSS-REFERENCE TO RELATED APPLICATIONS

This application relates to co-pending U.S. patent application Ser. No. 09/727,530, entitled "System and Method for Real-Time Library Generation of Grating Profiles" by Jakatdar, et al., filed on Nov. 28, 2000, to co-pending U.S. patent application Ser. No. 09/907,488, entitled "Generation of a Library of Periodic Grating Diffraction Signals" by Niu, et al., filed on Jul. 16, 2001, and to co-pending U.S. patent application (number to be assigned) entitled "Metrology Diffraction Signal Adaptation for Tool-to-Tool Matching" by Laughery, et al., filed on Mar. 29, 2002, all owned by the assignee of this application and incorporated herein by reference.

BACKGROUND

1. Field of the Invention

The present invention is directed to integrated circuit metrology methods and apparatuses, and more particularly to augmentation of projection microscopy methods and apparatuses with optical profilometry methods and apparatuses, and augmentation of optical profilometry methods and apparatuses with projection microscopy methods and apparatuses.

2. Related Art

As the scale of semiconductor devices decreases, control of the profile of the features of integrated circuit structures formed on semiconductor wafers becomes increasingly difficult. Yet to insure high throughput of circuits that perform according to design, it is desirable to obtain the profiles of features of integrated circuit structures, and particularly their critical dimensions.

The profile of structures formed on a wafer can be obtained using projection microscopy, such as critical dimension scanning electron microscopes/microscopy (CD-SEM). In a typical CD-SEM system, images are produced by an electron beam's transmission through the structures formed on the semiconductor wafer. However, refraction and reflections of the beam from surfaces of the structures can cause distortions in the CD-SEM image.

SUMMARY

In one embodiment, a metrology method and system of structures on a wafer includes obtaining a projection image of at least a first portion of the structures on the wafer using a first metrology apparatus. A profile of at least a second portion of the structure on the wafer is obtained using a second metrology apparatus. The information from the profile obtained using the second metrology apparatus and the information from the projection image obtained using the first metrology apparatus are combined using a processor.

DESCRIPTION OF DRAWING FIGURES

The present invention can be best understood by reference to the following description taken in conjunction with the accompanying drawing figures, in which like parts may be referred to by like numerals:

Figure 4:
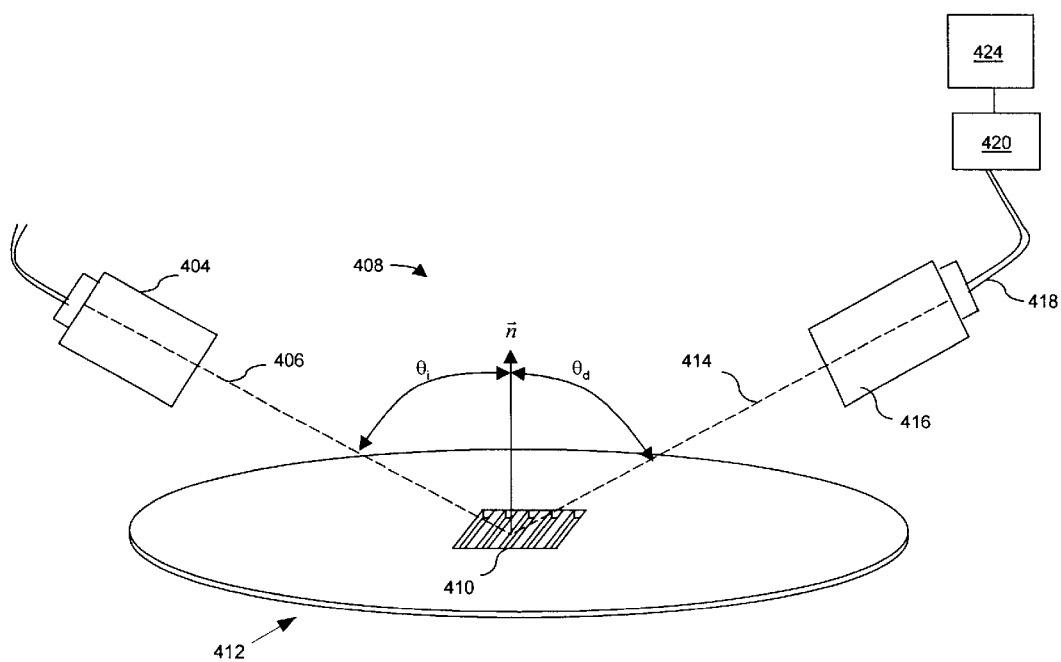

FIG. 4 an architectural diagram illustrating an exemplary scatterometer.

Figure 5:
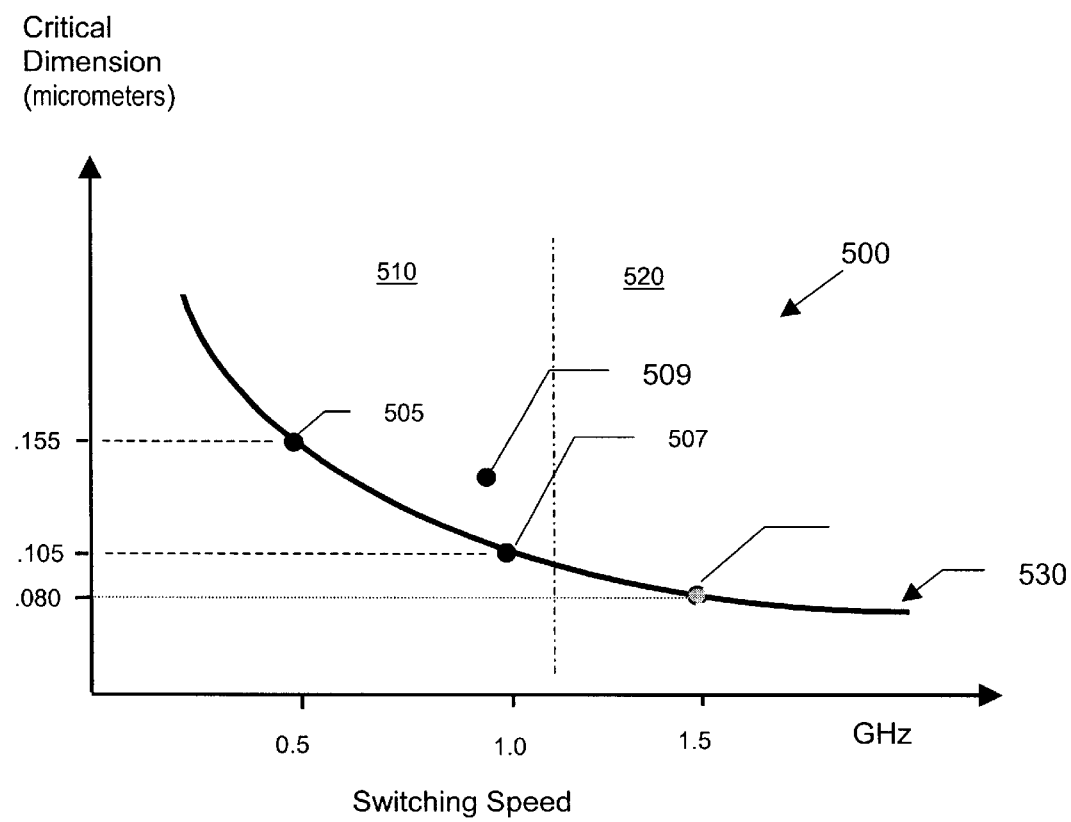

FIG. 5 shows a graph of switching speed versus critical dimension.

Figure 6A:
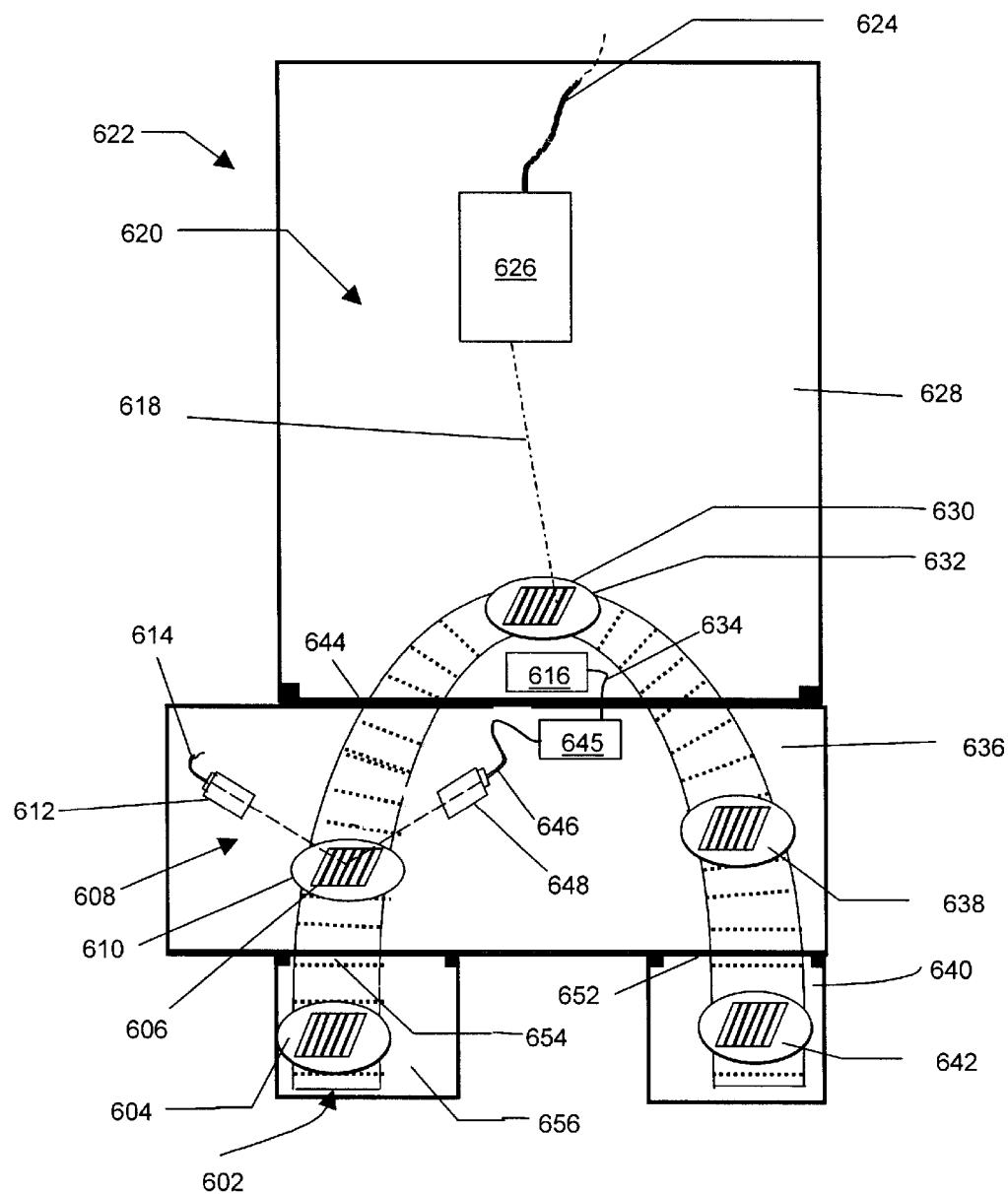

FIG. 6A is an architectural diagram illustrating an exemplary wafer metrology system.

Figure 6B:
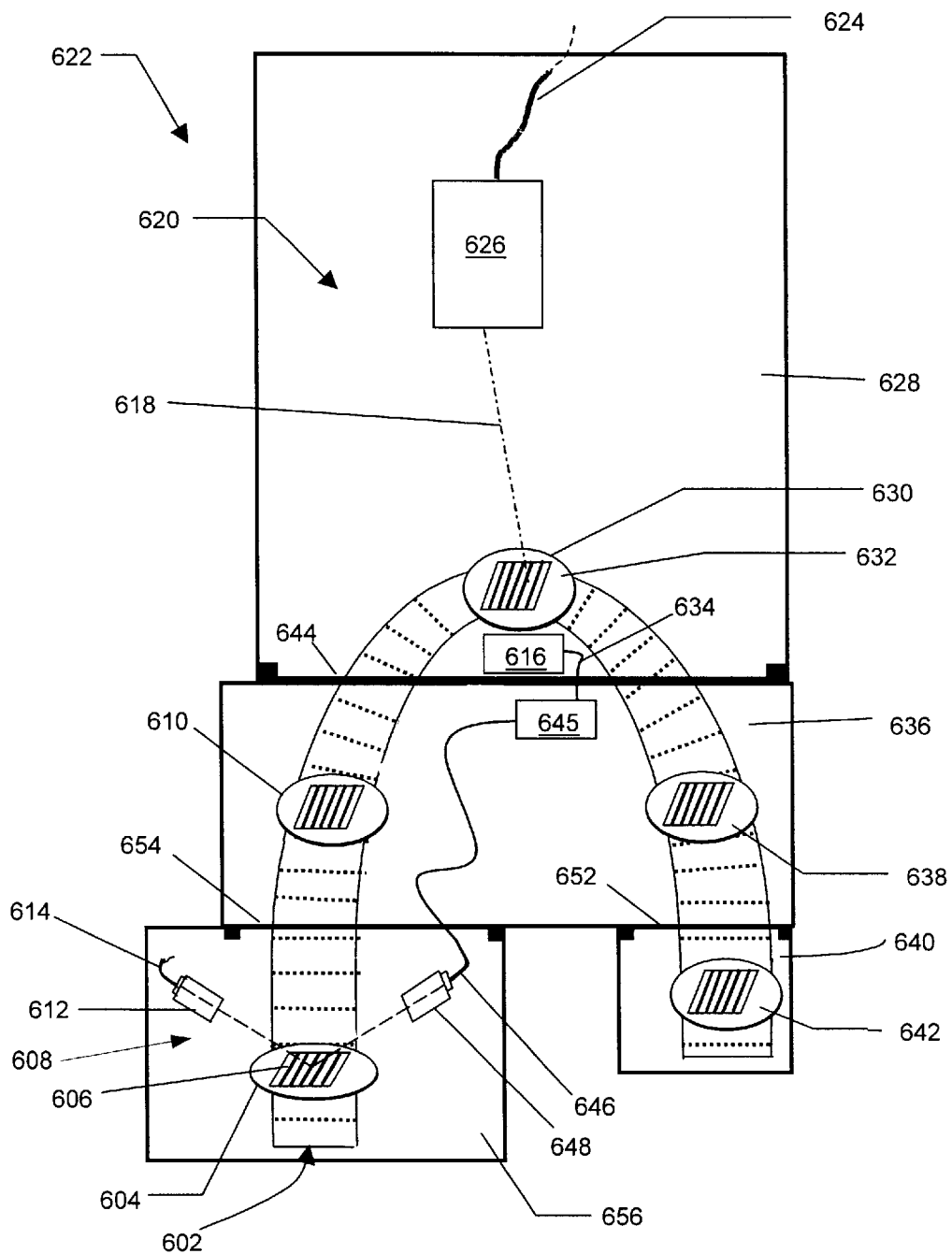

FIG. 6B is an architectural diagram illustrating another exemplary metrology system.

Figure 6C:
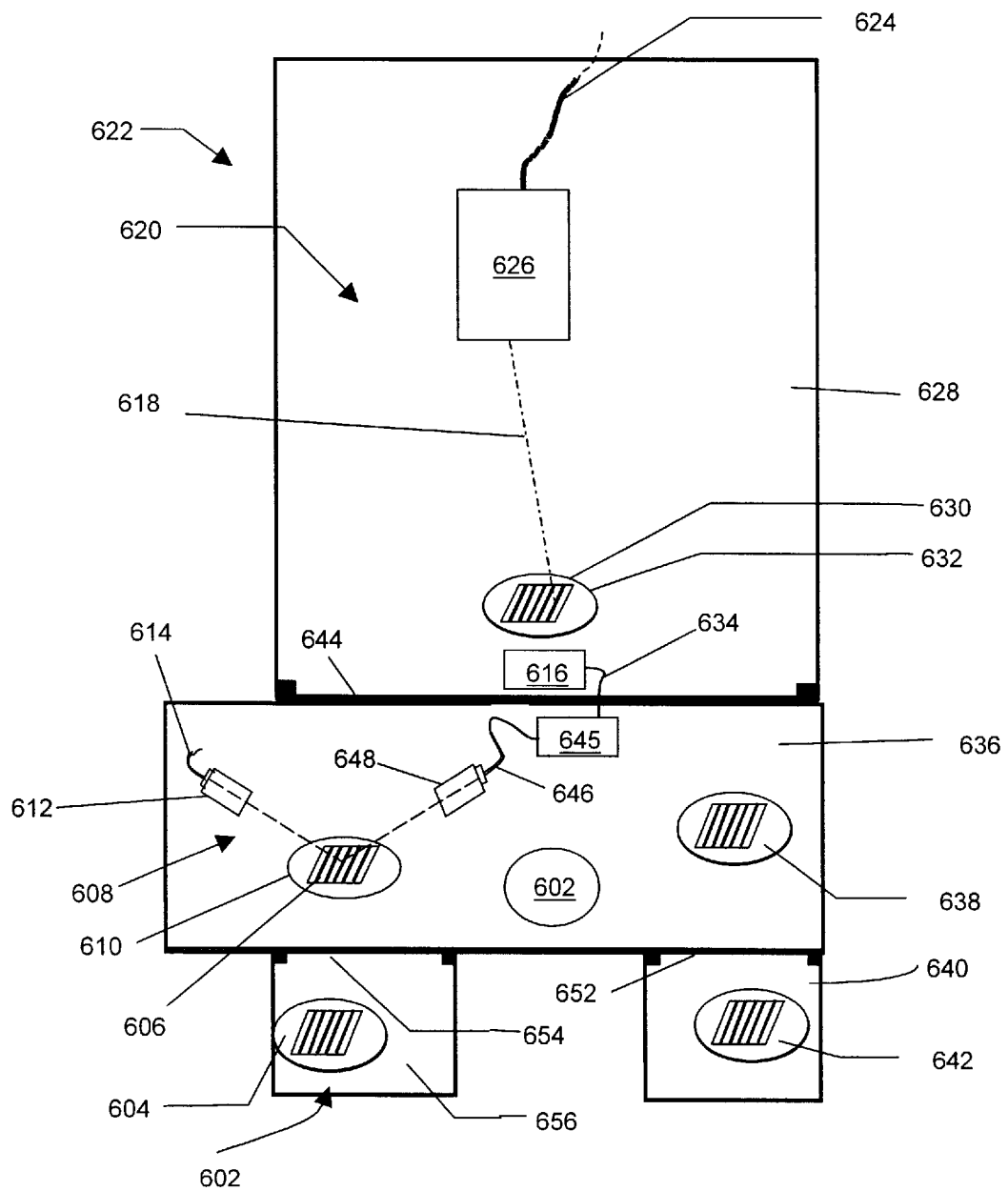

FIG. 6C is an architectural diagram illustrating another exemplary metroloy system.

Figure 7A:
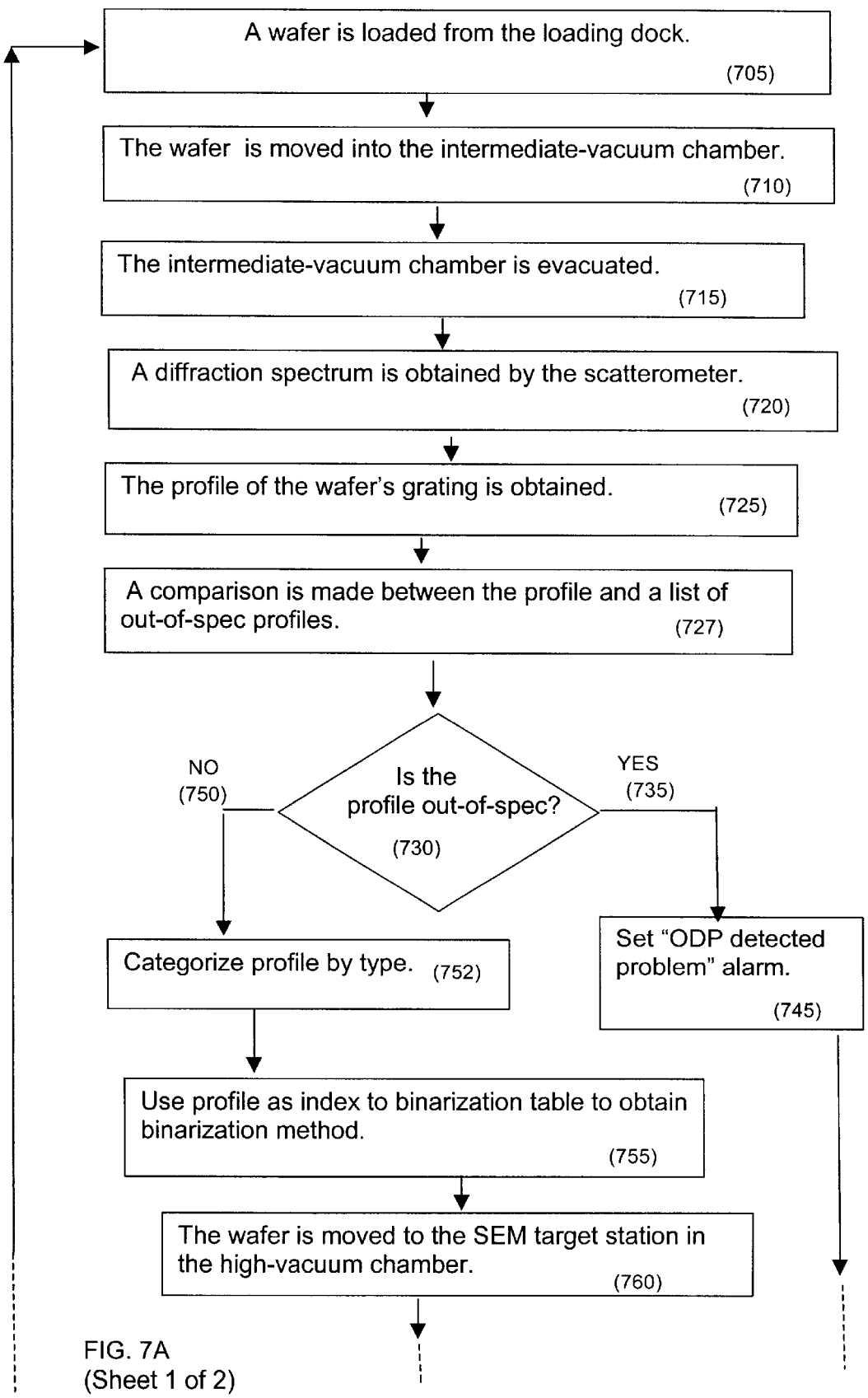
Figure 7A:
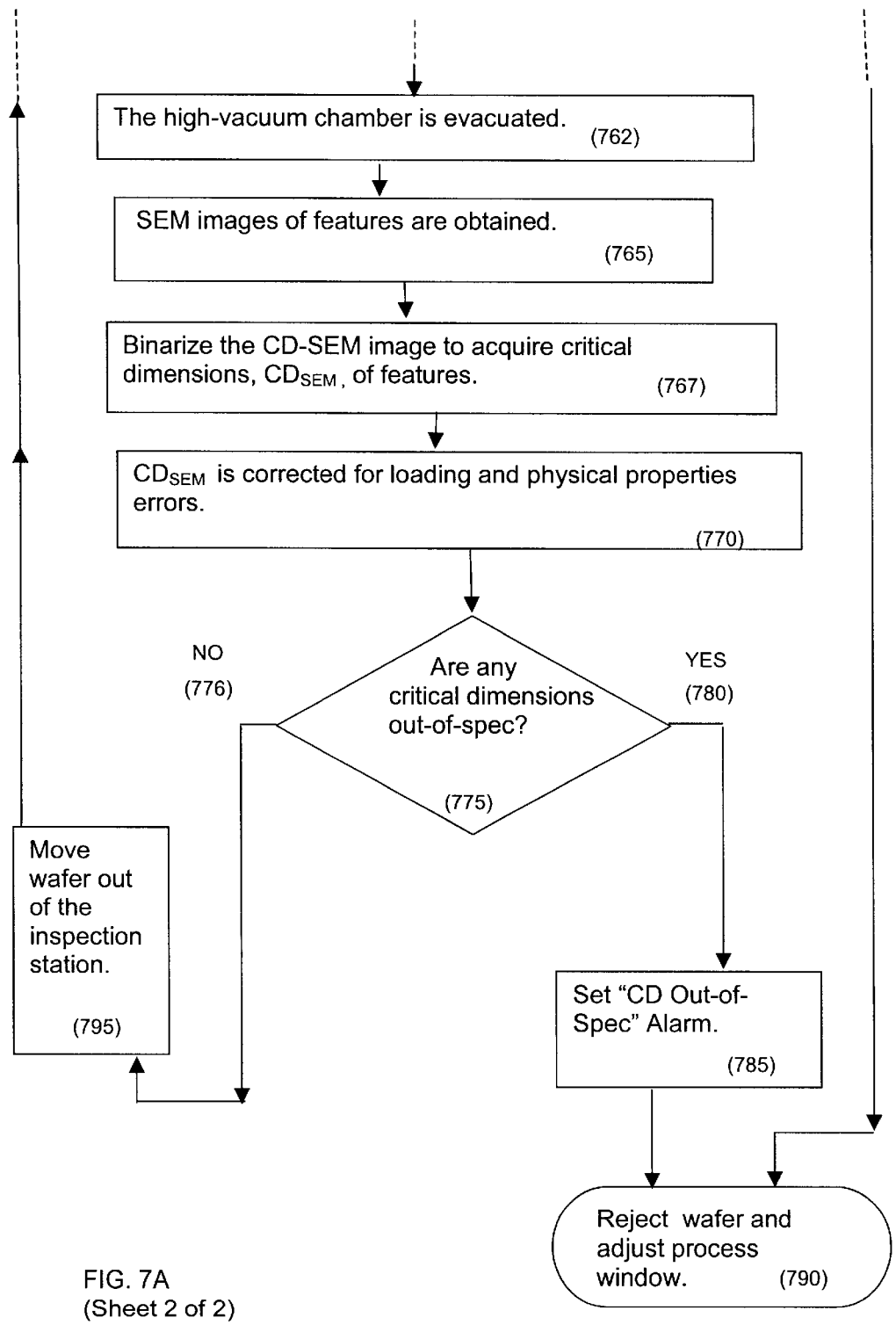

FIG. 7A depicts an exemplary process for the use of an exemplary wafer metrology system.

FIG. 7B shows an exemplary binarization table.

Figure 8A:
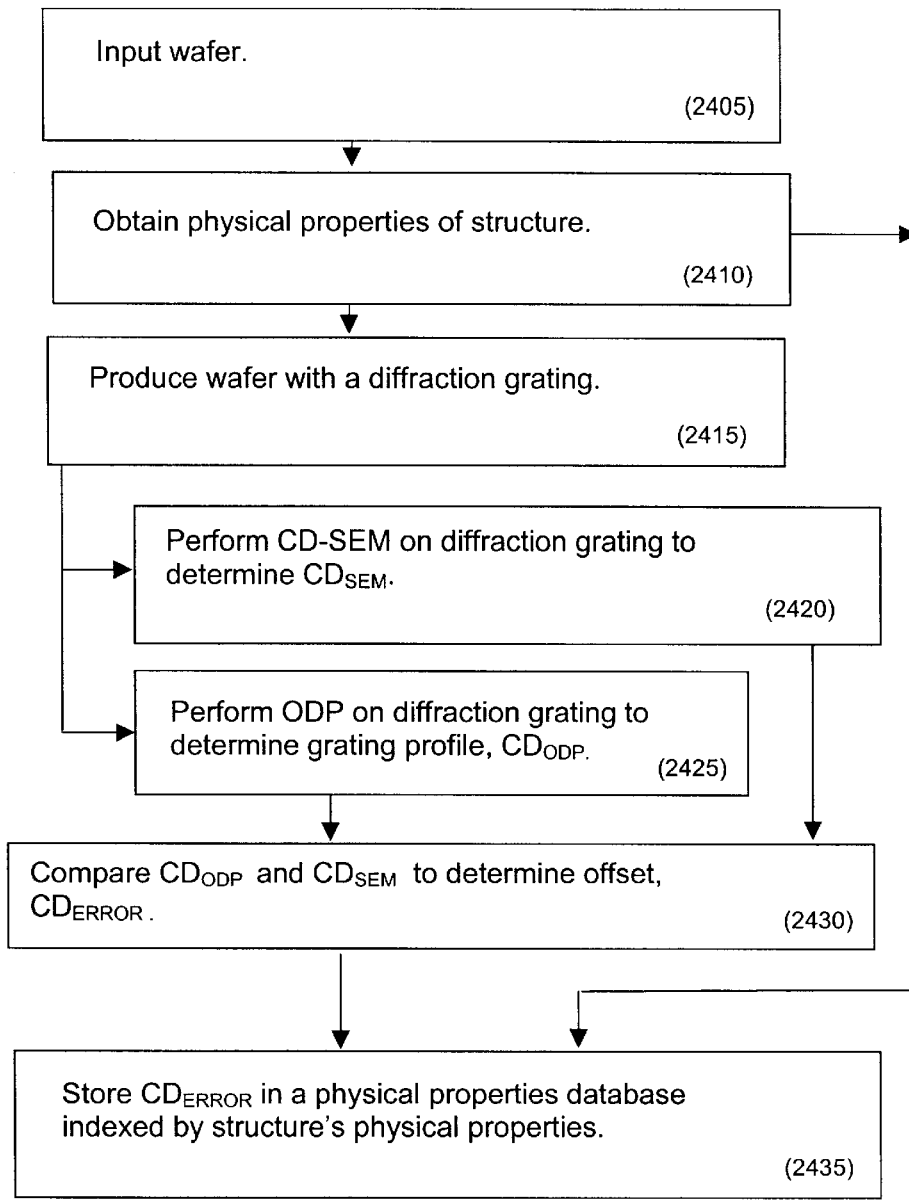

FIG. 8A depicts an exemplary process for the use of a CD-SEM physical property errors database.

Figure 8B:
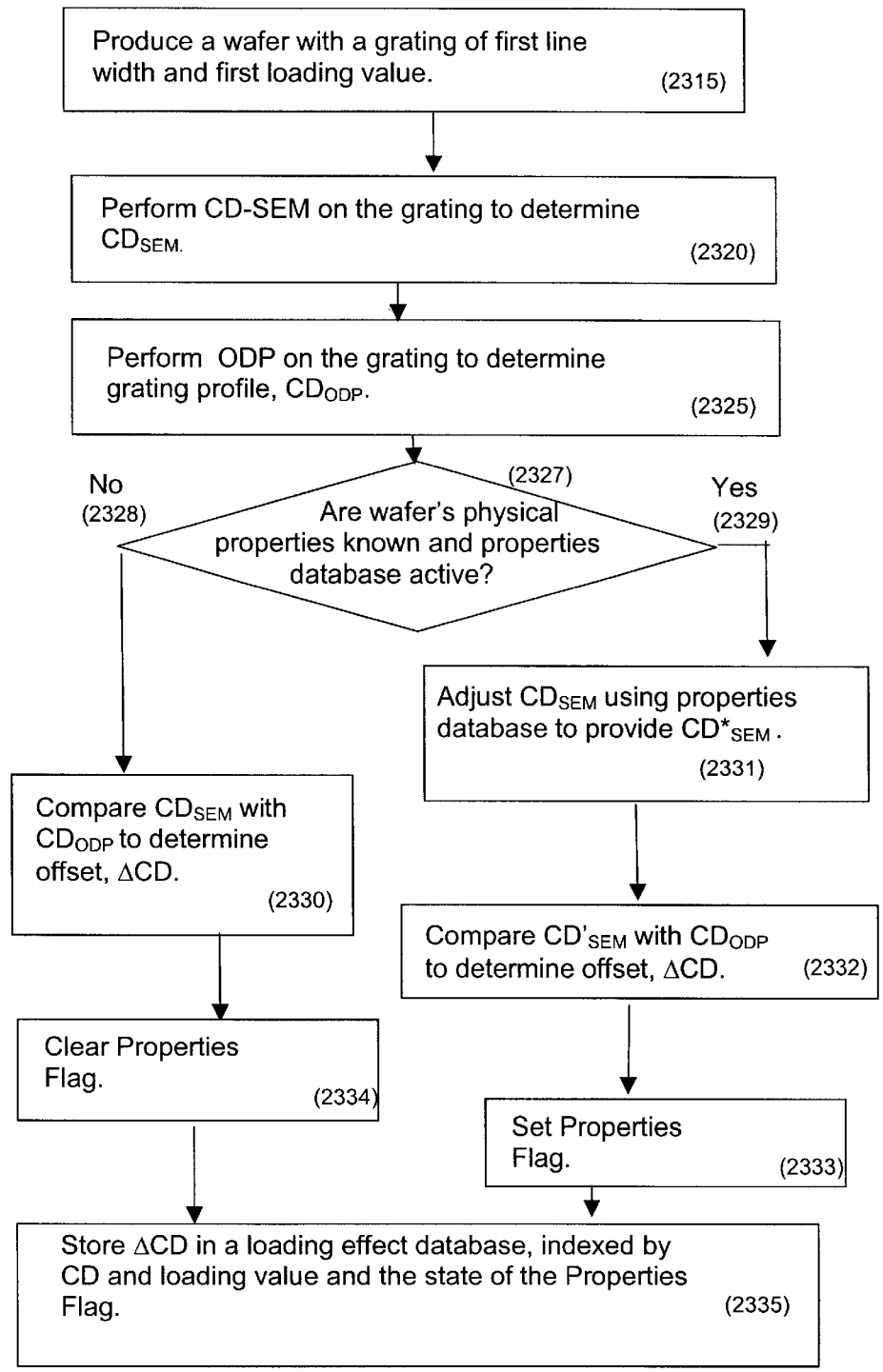

FIG. 8B depicts an exemplary process for the use of a CD-SEM loading effect database.

Figure 8C:
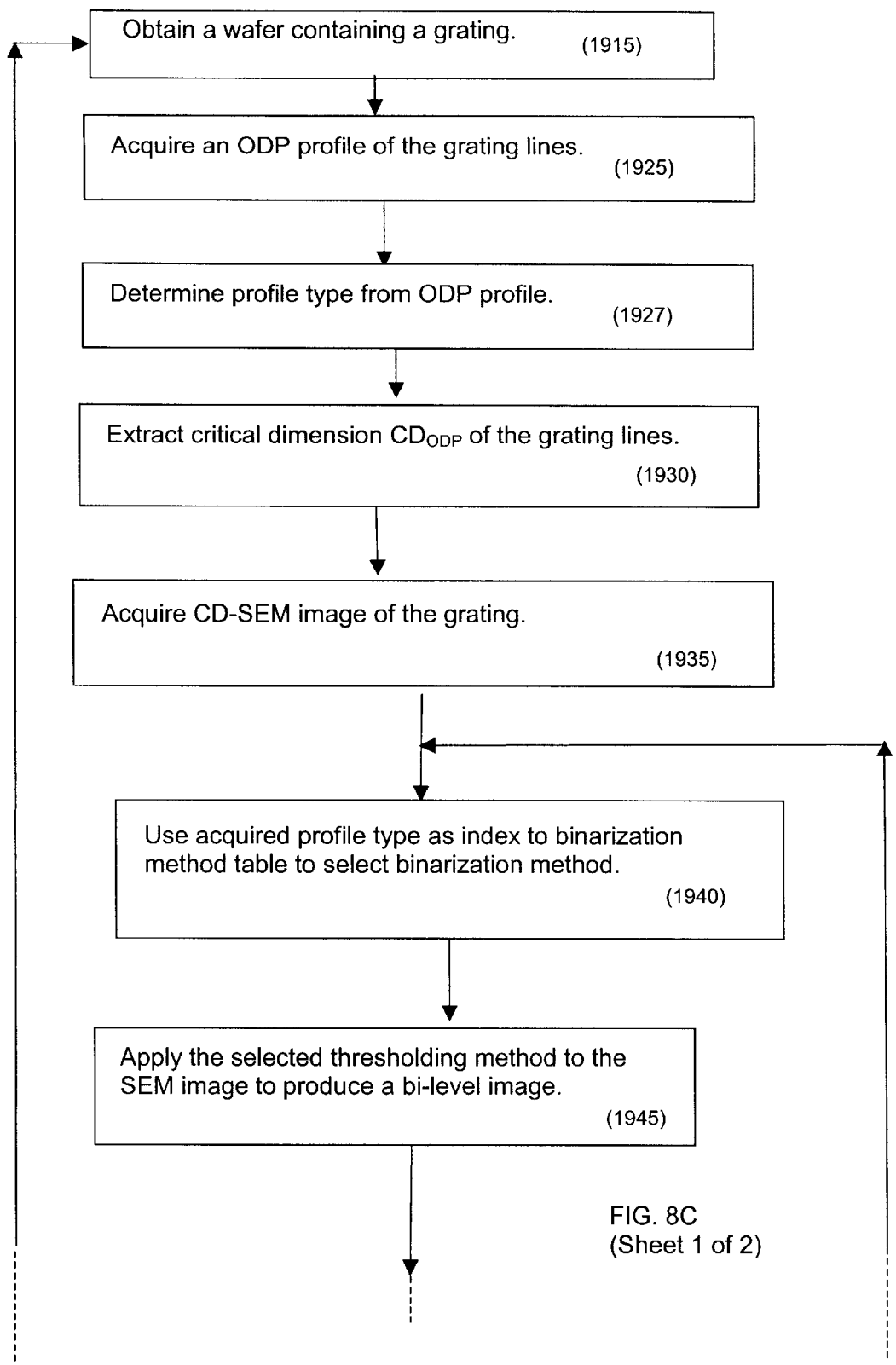
Figure 8C:
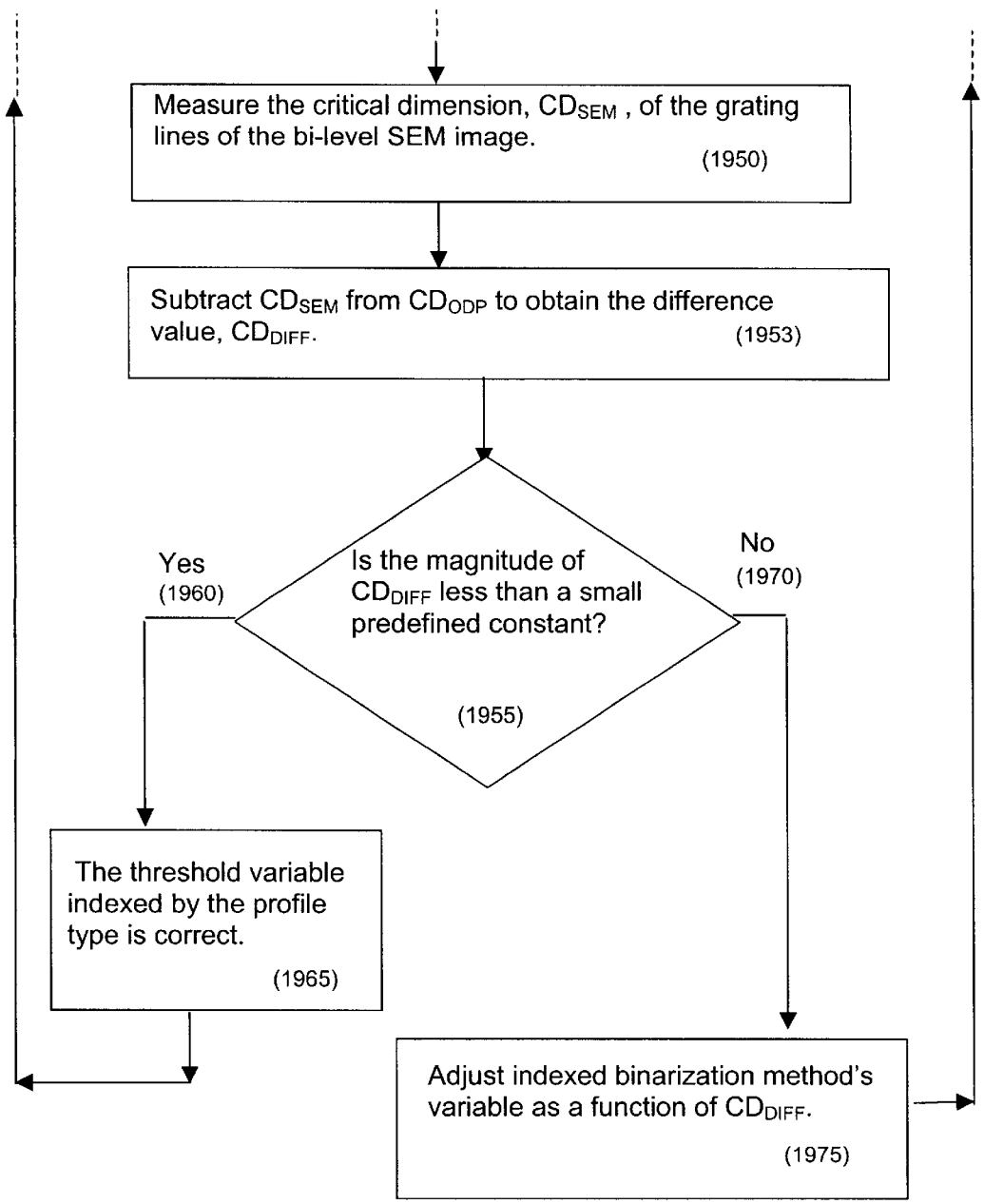

FIG. 8C depicts an exemplary process for applying a binarization to SEM image data to adjust variables in a binarization table.

Figure 9:
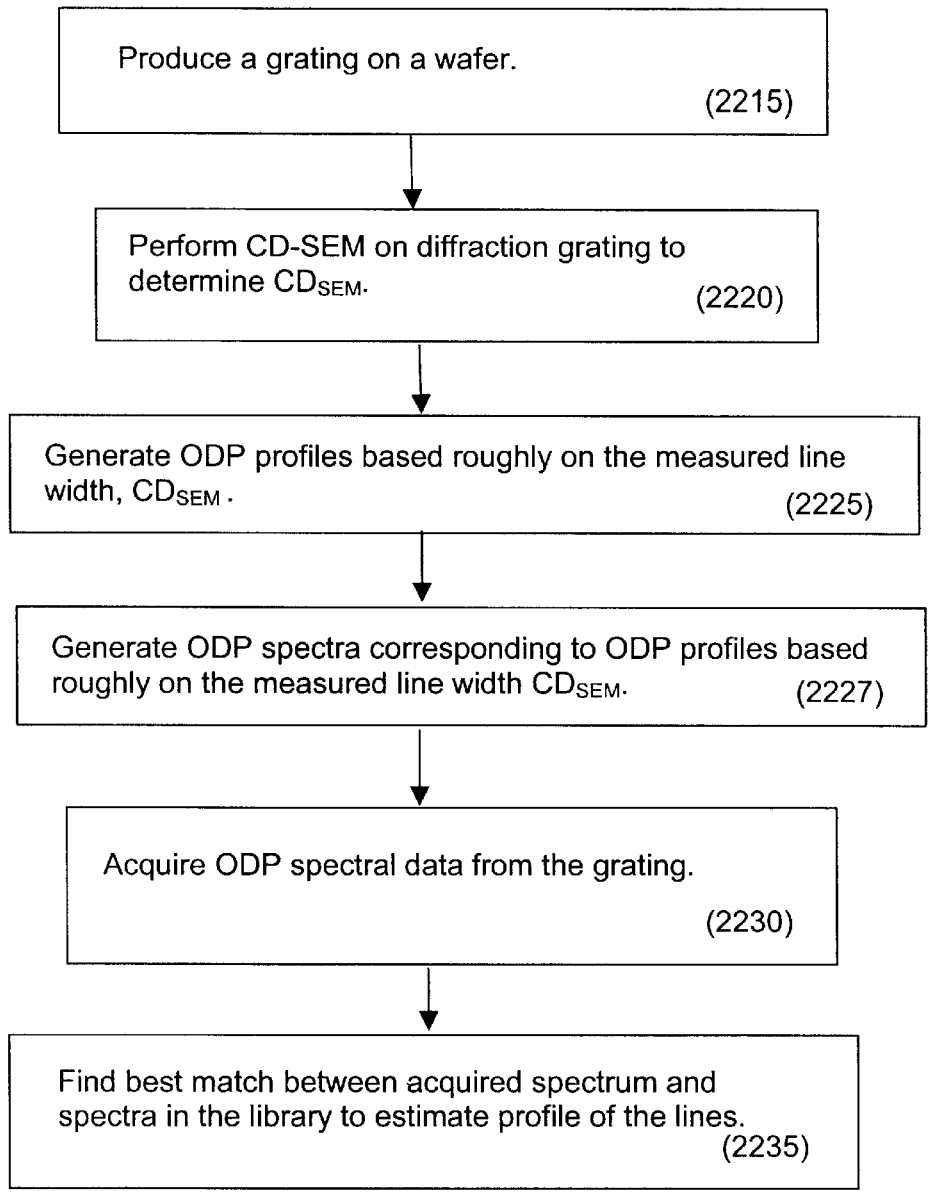

FIG. 9 depicts an exemplary process for the use of CD-SEM data as initial data for OP profile/spectrum library generation.

Figure 10:
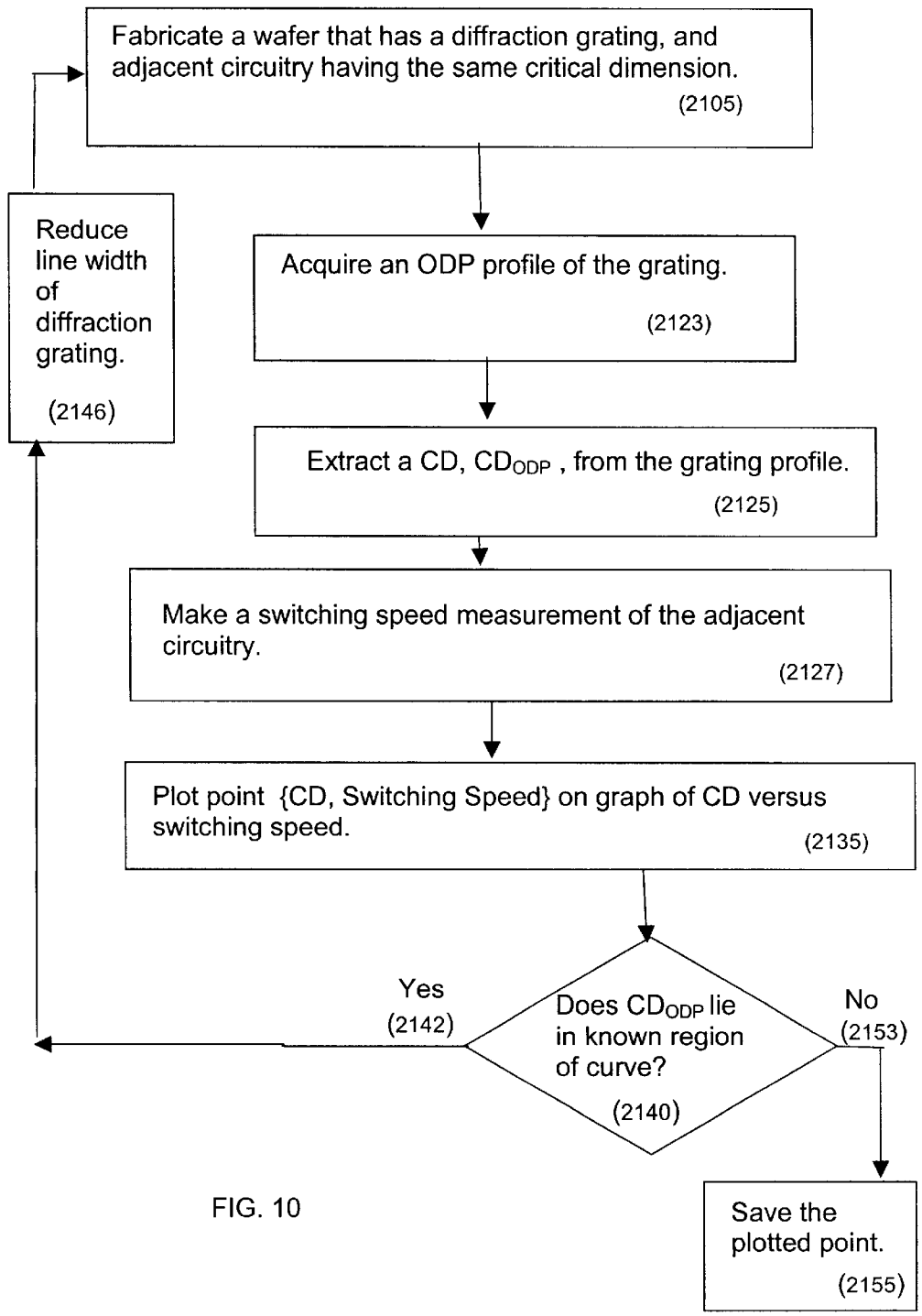

FIG. 10 depicts an exemplary process for the generation of speed versus critical dimension graph points.

Figure 11:
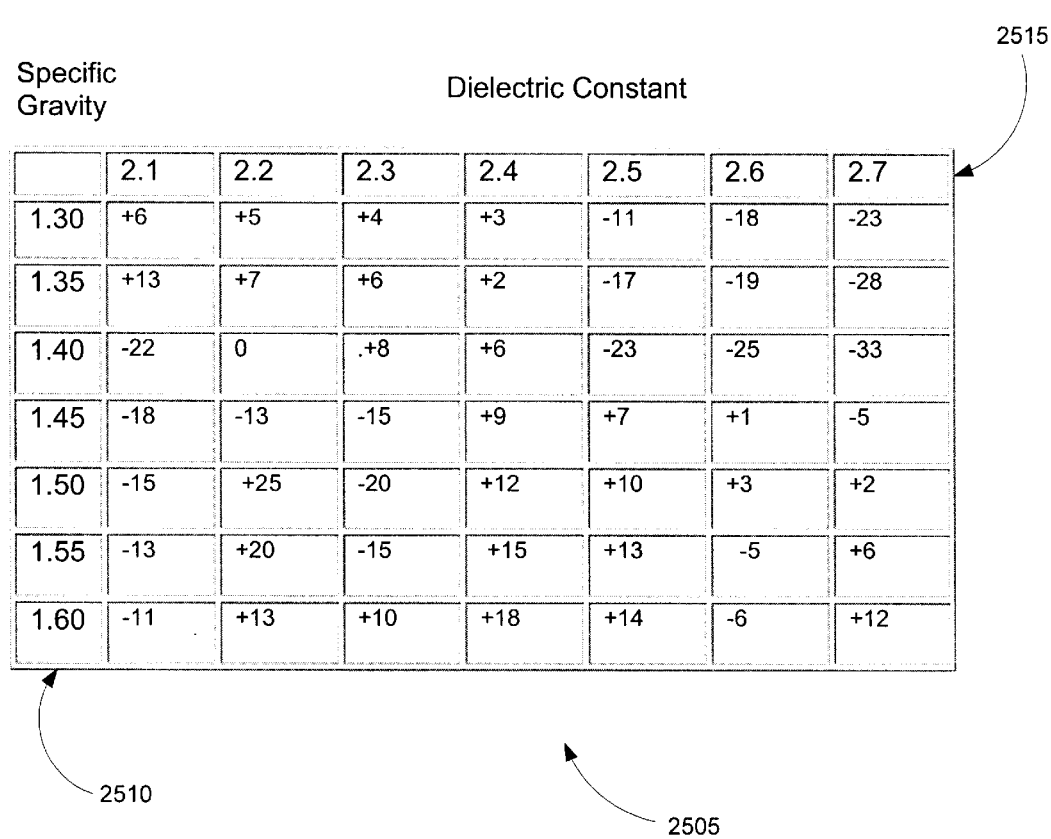

FIG. 11 shows an exemplary CD-SEM physical property errors database.

FIG. 12 shows an exemplary CD-SEM loading effect database.

DETAILED DESCRIPTION

The following description sets forth numerous specific configurations, parameters, and the like. It should be recognized, however, that such description is not intended as a limitation on the scope of the present invention, but is instead provided as a description of exemplary embodiments.

1. A Combined Optical Profilometry and Projection Microscopy Wafer Metrology System FIG. 6A depicts an exemplary embodiment of a wafer metrology system 622 having an optical profilometry (OP) station 608 and a projection microscopy (PM) station 620. As will be described below in greater detail, OP station 608 is configured to obtain and provide a profile of a portion of the structures on the wafer, and PM station 620 is configured to obtain and provide a projection image of a portion of the structures on a wafer. A processor 645 is configured to combine the information from the profile obtained by OP station 608 with information from the projection image obtained by PM station 620.

In the present exemplary embodiment, OP station 608 includes a scatterometer. More specifically, as depicted in FIG. 6A, OP station 608 includes an excitation head 612, a target area 606, detector 648, input wires 614, and output wires 646. OP station 608 can be powered and controlled by input via input wires 614. The profiles obtained by OP station 608 can be transferred to processor 645 using output wires 646. It should be noted that OP station 608 can include various optical profilometry systems, such as an ellipsometer, a reflectometer, and the like.

FIG. 4 depicts an exemplary scatterometer 408 in greater detail. In exemplary scatterometer 408, an incident beam 406 is generated by an excitation head 404 and directed at a wafer 412 having a diffraction grating 410. Incident beam 406 can include radiation having two polarizations to allow measurement of both intensity and phase of the diffracted electromagnetic radiation 414 monitored by an optical detector 416. If scatterometer 408 of FIG. 4 is an ellipsometer, then diffracted radiation 414 is received by detector 416 and separated into two polarizations before passing the signal to a spectrometer 420 via an optical fiber 418. If scatterometer 408 of FIG. 4 is a reflectometer, the diffracted radiation 414 can be sent directly to spectrometer 420 via optical fiber 418. Spectrometer 420 can then send the signal to a signal processor 424. Spectrometer 420 can include a charge coupled device (not shown) or a photo-multiplier (not shown) that can convert optical signals to electrical signals.

Figure 1:
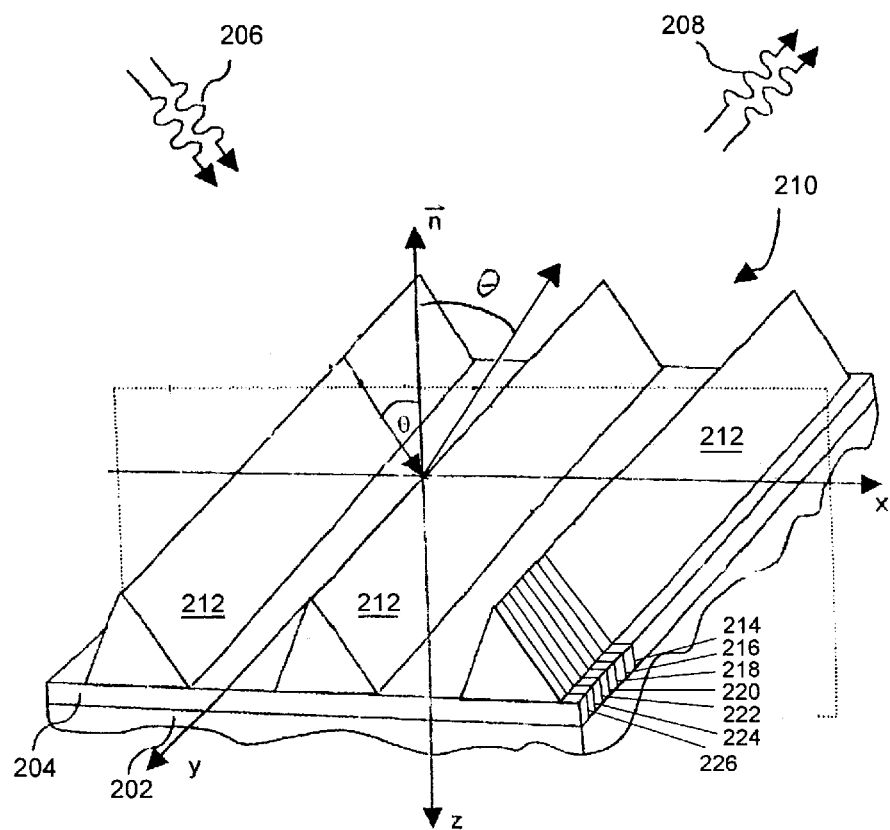
FIG. 1 illustrates a grating pattern on an integrated circuit wafer.

FIG. 1 depicts a section of a periodic grating with radiation 206 incident on the grating at an angle θ from the normal vector n, and radiation 208 diffracted from the grating at an angle θ on the other side of the normal vector n. The section of the grating that is depicted in FIG. 1 includes three ridges or lines 212, which are shown as having a triangular cross-section. In FIG. 1 the ridges 212 are atop a deposited film 204, and the film 204 is atop a substrate 202, which is considered to extend semi-infinitely in the +z direction. One or more periodic gratings can be formed in test areas on a wafer. The periodic gratings can be formed proximate to or within devices/circuits formed on the wafer.

A diffraction spectrum measured from the periodic grating can be used to obtain the profile of the periodic grating. More specifically, the measured diffraction spectrum can be compared to a library having sets of theoretically generated diffraction spectrum and profile pairs. The profile associated with the theoretically generated diffraction spectrum that most closely matches the measured diffraction spectrum can be determined to be the profile of the periodic grating. For a more detailed description, refer to co-pending U.S. patent application Ser. No. 09/907,488, entitled "Generation of a Library of Periodic Grating Diffraction Signals" by Niu, et al., filed on Jul. 16, 2001, which is incorporated herein in its entirety by reference, and co-pending U.S. patent application Ser. No. 09/727530, entitled "System and Method for Real-Time Library Generation of Grating Profiles" by Jakatdar, et al., filed on Nov. 28, 2000, which is incorporated herein in its entirety by reference.

In the present exemplary embodiment, PM station 620 includes a CD-SEM system. More specifically, as depicted in FIG. 6A, PM station 620 includes an electron beam generator 626, a target area 630, an electron beam detector 616, input wires 624, and output wires 634. PM station 620 is powered and controlled by input via input wires 624 and generates an electron beam 618. The projection images obtained by PM station 620 can be transferred to processor 645 using output wires 634. It should be noted that PM station 620 can include various projection microscopy systems, such as atomic force microscopy, ion beam microscopy, and the like.

With reference again to FIG. 6A, in the present exemplary embodiment, OP station 608 is housed within an intermediate-vacuum chamber 636, and PM station 620 is housed within a high-vacuum chamber 628. In one exemplary configuration, high-vacuum chamber 628 can be maintained at about 100 to 1000 millitorr, and intermediate-vacuum chamber 636 can be maintained at about 1 to 2 millitorr. It should be noted, however, that high-vacuum chamber 628 and intermediate-vacuum chamber 636 can be maintained at various vacuums, and that the relative terms high and intermediate indicate the relative pressure of high-vacuum chamber 628 to intermediate-vacuum chamber 636 rather than any particular amount of vacuum.

In the present exemplary embodiment, wafer metrology system 622 includes a loading dock 656 to load wafers to be processed, and a loading dock 640 to receive processed wafers. Although not depicted in FIG. 6A, additional automation mechanisms, such as conveyors or robotics, may be used to load wafers onto loading dock 656 and remove wafers from loading dock 640. Additional, wafers can be loaded onto dock 656 and removed from loading dock 640 manually. Furthermore, batches of wafers can be loaded onto loading dock 656 and removed from loading dock 640 in wafer cassettes.

Wafer metrology system 622 also includes sealing doors 644, 654, 652 that operate to maintain the vacuum within high vacuum chamber 628 and intermediate-vacuum chamber 636 as wafers are processed through wafer metrology system 622. As depicted in FIG. 6A, sealing doors 654 and 652 separate intermediate-vacuum chamber 636 from loading docks 656 and 640, respectively. Sealing door 644 separates high-vacuum chamber 628 from intermediate-vacuum chamber 636.

In the present exemplary embodiment, wafer metrology system 622 can operate to process multiple wafers through OP station 608 and PM station 620. For the sake of example, FIG. 6A depicts wafer metrology system 622 processing wafer 604, 610, 632, 638, and 642 at an instant of time. More particularly, wafers 604, 610, 632, 638, and 642 are depicted in loading dock 656, intermediate-vacuum chamber 636, high-vacuum chamber 628, and loading dock 640, respectively. Wafer 604 represents a wafer being held in loading dock 656 in preparation to be processed. Wafer 610 represents a wafer being examined at OP station 608. Wafer 632 represents a wafer being examined at PM station 620. Wafer 638 represents a wafer that has been examined by OP station 608 and PM station 620. Wafer 642 represents a wafer being held in loading dock 640 after being processed.

A transport device 602 can move wafers through wafer metrology system 622. For the sake of example, the movement and processing of a single wafer through wafer metrology system 622 will now be described. As such, assume that wafers 604, 610, 632, 638, and 642 now represent a single wafer at different times as it moves through wafer metrology system 622. The processing of a wafer begins when sealing door 654 is opened and transport device 602 moves the wafer to be processed (depicted as wafer 604) from loading dock 656 into intermediate-vacuum chamber 636. More particularly, transport device 602 positions the wafer to be examined (depicted as wafer 610) onto a targeting area 606 at OP station 608. As described above, at OP station 608, the profile of a periodic grating formed on the wafer is obtained. Sealing door 644 is then opened and transport device 602 moves the wafer from intermediate-vacuum chamber 636 into high-vacuum chamber 628. More particularly, transport device 602 positions the wafer to be examined (depicted as wafer 632) onto a targeting area 630 at PM station 620. As described above, at PM station 620, a projection image is obtained. Sealing door 644 is then opened and transport device 602 moves the wafer from high-vacuum chamber 628 into intermediate-vacuum chamber 636. Finally, sealing door 652 is opened and transport device 602 moves the examined wafer (depicted as wafer 638) from intermediate-vacuum chamber 636 into loading dock 640. The processed wafer (depicted as wafer 642) can then be removed from loading dock 640.

FIG. 6B depicts another exemplary embodiment of wafer metrology system 622 having PM station 620 and OP station 608. In the present exemplary embodiment, OP station 608 is housed within loading dock 656 rather than intermediate-vacuum chamber 636.

In FIG. 6A and FIG. 6B, transport device 602 has been depicted as a conveyor. It should be noted that transport device 602 can include various mechanisms to move wafers throughout wafer metrology system 622. For example, FIG. 6C depicts an exemplary embodiment of wafer metrology system 622 in which transport device 602 is configured as one or more robotic arms.

Using a Combined Optical Profilometry and Projection Microscopy Wafer Metrology System FIG. 7A depicts an exemplary process of operating a wafer metrology system that includes a combination of optical profilometry and projection microscopy. The exemplary process depicted in FIG. 7A can be implemented as a program in a computer system operating in the wafer metrology system. For the sake of convenience and clarity, the exemplary process depicted in FIG. 7A is described below in connection with the exemplary embodiment of wafer metrology system 622 depicted in FIG. 6A. It should be noted, however, that the exemplary process depicted in FIG. 7A can be used in connection with the exemplary embodiment of wafer metrology system 622 depicted in FIG. 6B and/or FIG. 6C, as well as various alternative embodiments.

In step 705, a wafer is obtained from the loading dock. In step 710, the wafer is moved into the intermediate-vacuum chamber. In step 715, the intermediate-vacuum chamber is evacuated. In step 720, a diffraction spectrum is measured from a periodic grating formed on the wafer. In step 725, the profile of the periodic grating is obtained from the measured diffraction spectrum. In step 727, a comparison is made between the obtained profile and a list of out-of-spec profiles. In step 730, a decision is made as to whether the obtained profile is out of spec.

In step 745, if the profile is found to be out-of-spec (branch 735), an OP-detected-problem alarm can be set. In step 790, the wafer is then rejected and the process window (i.e., the parameters of the fabrication process, such as focus, exposure, deposition rate, and the like) is adjusted.

In step 752, if the profile is found not to be out-of-spec (branch 750), the profile is categorized as to type. In step 755, the profile is used as an index to a binarization table. More particularly, FIG. 7B depicts an exemplary binarization table 1990 of exemplary profile types 1992 and exemplary binarization methods 1997. It should be noted, however, that binarization table 1990 can include various types of profile types and various binarization methods that can increase contrast, including those that maintain gray scales.

Figure 2:
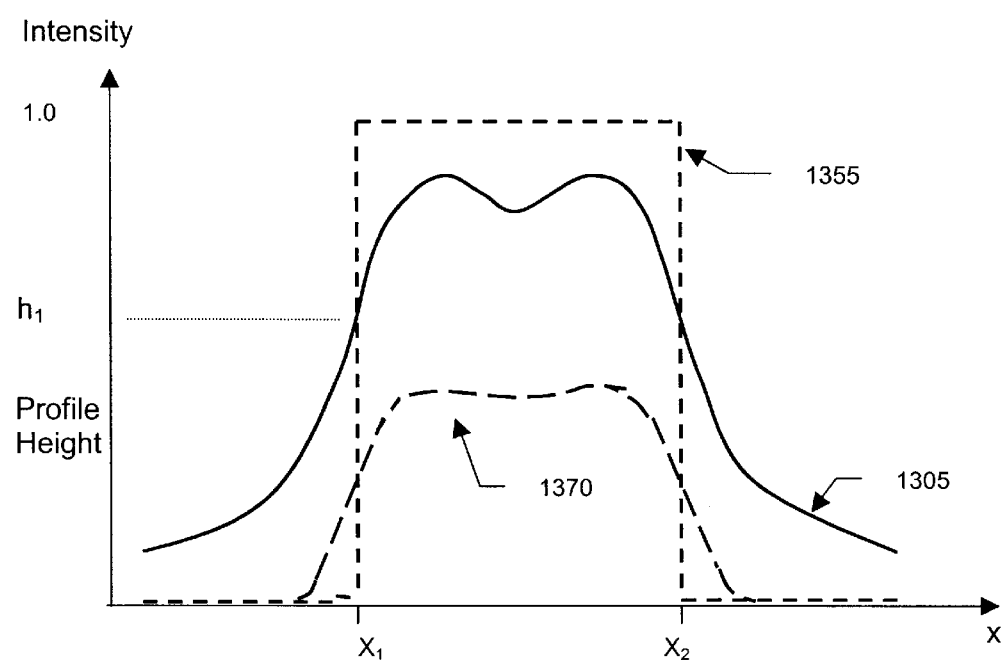
FIG. 2 shows plots of a structure profile, the intensity of an image of the structure, and a plot of a bi-level binarization of the intensity.

With reference again to FIG. 7A, in step 760, the wafer is moved to the SEM target station in the high-vacuum chamber. In step 762, the high-vacuum chamber is evacuated to produce a high vacuum level. In step 765, an SEM image is obtained. In step 767, a binarization is applied to the SEM image to obtain critical dimension, $CD_{SEM}$, of the structure. More particularly, FIG. 2 depicts an exemplary bi-level image 1355 of CD-SEM image 1305. The CD-SEM critical dimension, $CD_{SEM}$, can then be obtained from bi-level image 1355.

With reference again to FIG. 7A, in step 770, the CD-SEM critical dimension, $CD_{SEM}$, is corrected for loading and physical properties errors to produce an errors-corrected critical dimension, $CD'_{SEM}$. The errors-corrected critical dimension, $CD'_{SEM}$, is then compared to previously determined critical dimension acceptance criteria. In step 775, a decision is made as to whether the errors-corrected critical dimension, $CD'_{SEM}$, is out of specification.

In step 785, if the errors-corrected critical dimension, $CD'_{SEM}$, is out of specification (branch 780), then a critical dimension alarm can be set. In step 790, the wafer is then rejected and the process window (i.e., the parameters of the fabrication process, such as focus, exposure, deposition rate, and the like) is adjusted.

In step 795, if the errors-corrected critical dimension, $CD'_{SEM}$, is not out of specification (branch 776), then the wafer is moved out of the high-vacuum chamber. In step 705, another wafer can be loaded from the loading dock.

3. Calibration of CD-SEM with Optical Profilometry

As described above, in one exemplary embodiment, projection microscopy can include CD-SEM. As such, as described below, the profiles obtained using optical profilometry can be used to correct errors in CD-SEM images.

3.1 Physical property Error Corrections

The physical properties of the structure under investigation (such as conductivity, specific gravity, doping material, coefficient of thermal expansion, dielectric constant, etc., of each component of the structure) can affect the electron beam and hence the accuracy of CD-SEM imaging. Since some of these properties are known, or can be obtained, they can be used to calibrate a CD-SEM-determined critical dimension, $CD_{SEM}$, or correct for distortions in CD-SEM imaging.

FIG. 8A depicts an exemplary process to provide an entry in a database of physical property-dependent critical dimension corrections for CD-SEM imaging. In step 2405, a raw wafer material is input into the system. In step 2410, the physical properties of structural components are obtained. In step 2415, a wafer with a diffraction grating is produced.

In step 2420, the structure is measured with a CD-SEM to obtain a CD-SEM critical dimension measurement, $CD_{SEM}$. In step 2425, optical profilometry is performed on a diffraction spectrum acquired from the grating to obtain an OP critical dimension, measurement, $CD_{OP}$. The order of performing the CD-SEM critical dimension measurement 2420 and the OP critical dimension measurement 2425 can be varied. In step 2430, the CD-SEM critical dimension, $CD_{SEM}$, and the OP critical dimension measurement, $CD_{OP}$, are then compared to determine a critical dimension offset $CD_{ERROR}$. In step 2435, the critical dimension offset $CD_{ERROR}$ is stored in the physical properties database, indexed by the structures's physical properties.

FIG. 11 depicts an exemplary physical property errors database 2505 with specific gravity values in the left-hand column 2510 and the dielectric constant values in the top row 2515. An exemplary properties database entry is indexed by, for instance, a specific gravity of 1.50 and a dielectric constant of 2.2, yielding a resultant $CD_{ERROR}$ of +25. Each physical property errors database entry is shown in units of nanometers, but could alternatively be expressed in terms of a percentage, or other units. The structure of the database, including the number of indices and the level of quantization, can be determined by the use of well-known statistical methodologies (such as linear extrapolation, least-squares best fit, etc.), and can include as many indices as there are significant and obtainable physical properties. It should be noted that other physical properties (such as conductivity, specific gravity, dielectric constant, doping material, heat capacity, coefficient of thermal expansion, tensile strength, compressibility, resilience, etc.) may also be acquired and used to correct for physical property-dependent errors. Furthermore, the number of properties used as indices to the physical property errors database may be less than or greater than two.

Note also that an image of a structure may be considered to be a superposition of a series of closely spaced profiles of the structure. For example, FIG. 1 depicts a series of closely-spaced x,z-plane "cuts" 214, 216, 218, 220, 222, 224 and 226 across the rightmost ridge 212. The outline of each cut 214, 216, 218, 220, 222, 224 and 226 provides a profile (also referenced in this paragraph with numerals 214, 216, 218, 220, 222, 224 and 226) of the ridge 212 having a triangular peak. Mapping the height along the z-axis of each profile 214, 216, 218, 220, 222, 224 and 226 to a gray-scale value projected onto the x-y plane provides a two-dimensional image of the ridge 212, which will not generally be triangular. Therefore, once the critical dimension offset $CD_{ERROR}$ is determined for a structure, or a portion of a structure, according to the above-described process depicted in FIG. 8A, the critical dimension offset $CD_{ERROR}$ can be applied to a series of closely-spaced profiles corresponding to the image of the structure to provide a correction to the image.

3.2 Loading Effect Error Corrections

Another cause of inaccuracy in CD-SEM measurements can be "loading effect." The loading effect can be produced by multiple reflections of electrons from the electron beam off the surfaces of the structures under investigation. Therefore, as the structures and the features within the structures become increasingly close together, loading effect distortions increase. For a simple single-component grating, the loading effect can depend on the density of lines and the line widths. In one exemplary embodiment, a loading effect database can be developed and used to correct raw CD-SEM measurements and distortions in CD-SEM images.

FIG. 8B depicts an exemplary process to provide an entry for a database of line width-dependent and density-dependent critical dimension corrections for CD-SEM imaging. Note that alternative sequences of steps may also be used to generate the loading effect database. In step 2315, a diffraction grating having a first line width and a first line density is produced on a wafer. In step 2320, a CD-SEM is performed to obtain a CD-SEM critical dimension measurement, $CD_{SEM}$. In step 2325, optical profilometry is performed on a diffraction spectrum acquired from the grating to obtain an OP critical dimension measurement, $CD_{OP}$. Note that the order of performing the CD-SEM critical dimension measurement (step 2320) and obtaining the OP critical dimension measurement (step 2325) can be varied.

In step 2327, a determination is then made as to whether the wafer's physical properties are known and the physical property errors database 2505 (FIG. 11) is active. In step 2331, if the wafer's physical properties are known and if the physical properties database is active (branch 2329), then the CD-SEM critical dimension measurement $CD_{SEM}$ is adjusted as discussed above in reference to the flowchart of FIG. 8A, and the physical property errors database 2505 (FIG. 11) is used to provide the physical properties adjusted CD-SEM critical dimension measurement, $CD'_{SEM}$. In step 2332, the adjusted CD-SEM critical dimension measurement $CD'_{SEM}$ and the OP critical dimension measurement $CD_{OP}$ are then compared to determine a critical dimension offset, $\Delta CD$. In step 2333, the properties flag is set.

However, in step 2330, if the wafer's physical properties are not known or if the physical properties database is not active (branch 2328), then the CD-SEM critical dimension measurement $CD_{SEM}$ is compared directly to the OP critical dimension measurement $CD_{OP}$. In step 2334, the properties flag is not set.

After the critical dimension offset $\Delta CD$ is found and the properties flag is set or not set (steps 2330 and 2334 or 2332 and 2333), in step 2335, the critical dimension offset $\Delta CD$ is stored in a loading effect database indexed by OP critical dimension measurement $CD_{OP}$, the density of lines, and the state of the properties flag.

FIG. 12 depicts an exemplary portion of a loading effect database 2605. Loading effect database 2305 has two table pages 2607 and 2608. One page 2607 is accessed when the properties flag state is set in step 2333 (FIG. 8B), and the other page 2608 is accessed when the properties flag is not set in 2334 (FIG. 8B). Note that diamond symbols in database 2605 indicate physically impossible combinations of density and critical dimension. Each cell entry, $\Delta CD$, is shown in units of nanometers, but could alternatively be expressed in terms of a percentage or other units. With the properties flag set in step 2333 (FIG. 8B), the cell indexed by a $CD_{OP}$ value of 200 nanometers and density value of 2.0 lines per micron has a value of +16 nanometers in this page 2607 of the exemplary database 2605.

As discussed above in connection with the process of FIG. 8A, an image of a structure may be considered to be a superposition of a series of closely spaced profiles of the structure. For example, FIG. 1 depicts a series of closely spaced x,z-plane "cuts" 214, 216, 218, 220, 222, 224 and 226 across the rightmost ridge 212. Mapping the height along the z-axis of each cut 214, 216, 218, 220, 222, 224 and 226 to a gray-scale value projected onto the x-y plane provides a two-dimensional image of the ridge 212. Therefore, once the critical dimension offset $\Delta CD$ is determined for a structure, or a portion of a structure, according to the above-described process depicted in FIG. 8B, the critical dimension offset $\Delta CD$ can be applied to a series of closely-spaced profiles corresponding to the image of the structure to provide a correction to the image.

3.3 Binarization Corrections

As described above, in FIG. 7A, in step 755, an SEM image can be binarized using a binarization method selected from binarization table 1990 (FIG. 7B) using the profile type as an index. Since a CD-SEM image can be affected by the underlying structure in complex ways, an OP-profile-selected binarization can increase the accuracy of the bi-level image for purposes of obtaining CD-SEM-derived critical dimensions.

As described above, FIG. 7B depicts an exemplary binarization table 1990. Binarization table 1990 is an N-row by two-column table, where N is the number of profile types into which profiles are categorized. Index column 1992 contains the profile types: T-top, footer, hourglass, triangular, square, convex top, concave top. These index profile types are descriptive of several of the broad grating-profile classes typically found in wafer fabrication. In binarization table 1990, binarization method column 1997 includes three types of binarizations. For instance, according to the binarization table 1990 of FIG. 7B, the profile type "footer" indexes the "fixed" binarization. Similarly, T-top and hourglass and square index maximum/minimum; triangular and concave index fixed; and convex top index inflection point.

Figure 3:
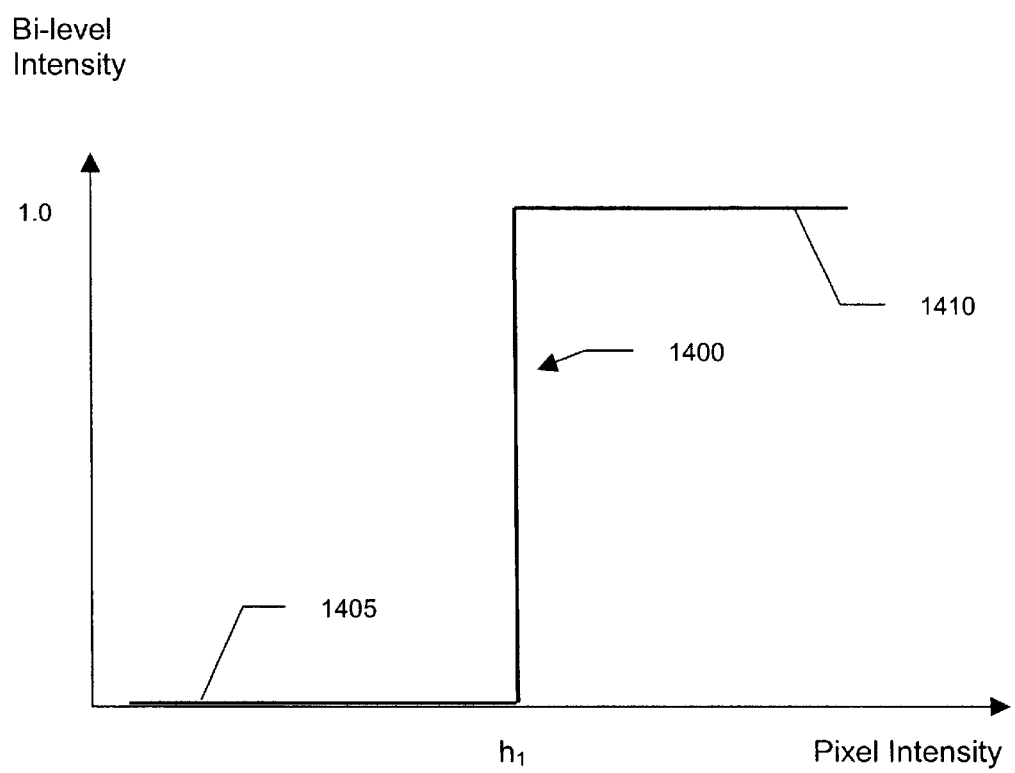
FIG. 3 is a plot of a binarization function.

In one exemplary embodiment, a "fixed" binarization process can set the binarization thresholds of the image intensity function $P(x)$ at a height, $h_1$, i.e., $$P(x_1)=h_1 \text{ and } P(x_2)=h_1, \tag{1.00}$$

and the critical dimension measurement can be given by $|x_2-x_1|$. FIG. 3 depicts a plot 1400 of a fixed binarization function 1400 having a threshold value of $h_1$. The binarization function 1400 maps pixel intensity values to bi-level intensity values. Pixels in the SEM image that have values equal to or above the binarization threshold $h_1$ are set to a value of unity, while pixels in the SEM image that have values below the binarization threshold $h_1$ are set to zero.

In the present exemplary embodiment, a "maximum/minimum" binarization process can set the thresholds at a predetermined ratio $\gamma$ between the maximum $P(x_{max})$ and minimum $P(x_{min})$ of the image intensity function $P(x)$, i.e., $$P(x_1)=\gamma h_2+P(x_{min}) \text{ and } P(x_2)=\gamma h_2+P(x_{min}), \qquad (1.20)$$

where $h_2=P(x_{max})-P(x_{min})$, $\gamma$ is an adjustable threshold ratio, and the critical dimension measurement is given by $|x_2-x_1|$.

Additionally, in the present exemplary embodiment, an "inflection point" binarization process can set the binarization thresholds based on the value of second derivatives of the image intensity function $P(x)$, i.e., $$\left.\frac{d^2P}{dx^2}\right|_{x=x_1} = \alpha \text{ and } \left.\frac{d^2P}{dx^2}\right|_{x=x_1} = \alpha \qquad (1.40)$$

where $\alpha$ is an adjustable threshold value, and the critical dimension measurement is given by $|x_2-x_1|$. It is noted that when $\alpha$ is assigned a value of zero, the inflection points of the image intensity function $P(x)$ are selected by equations (1.20) and (1.40).

FIG. 2 depicts a cross-sectional profile of a "concave top" profile type having a CD-SEM image 1305 that exhibits some distortions relative to the profile. A bi-level plot 1355 of the intensity of the profile is also shown. The bi-level plot 1355 can be obtained by application of the "fixed" binarization function T to the SEM cross-sectional pixel plot 1305, i.e., for a pixel with an intensity of p, the bi-level intensity of that pixel is given by T(p). The difference between the two points, $x_1$ and $x_2$, where the CD-SEM image 1305 reaches a value of $h_1$ provides the critical dimension, $CD_{SEM}$.

FIG. 8C depicts an exemplary process to refine the binarization table 1990 of FIG. 7B. In step 1915, a wafer containing a diffraction grating is first obtained from a production batch, or an individual test sample is used. In step 1925, an OP profile of the grating lines is then obtained. In step 1927, the profile type (column 1992 of FIG. 7B) is determined from the OP profile. In step 1930, a critical dimension, $CD_{OP}$, is extracted from the profile. In step 1935, a CD-SEM image of the grating is acquired. In step 1940, the grating profile type (column 1992 of FIG. 7B) is used as an index to binarization table 1990 (FIG. 7B) to select a binarization method 1997 (FIG. 7B). In step 1945, the selected binarization method 1997 (FIG. 7B) is then applied to raw SEM image 1305 (FIG. 2) to produce bi-level image1355 (FIG. 2) of the grating. In step 1950, the CD-SEM-derived critical dimension, $CD_{SEM}$, is then obtained from the bi-level image and subtracted 1953 from $CD_{OP}$ to obtain the difference value, $CD_{DIFF}$. In step 1975, if the magnitude of $CD_{DIFF}$ is determined not to be less than a small predefined constant $\delta$ (branch 1970), then the binarization table entry, 1992 of FIG. 7B, is modified.

According to the present invention, the selected binarization's variable $h_1$, $\gamma$, or $\alpha$, for the cases of fixed binarization, maximum/minimum binarization or inflection point binarization, respectively, can be adjusted as a function of $CD_{DIFF}$. For instance, the binarization's variable $h_1$, $\gamma$, or $\alpha$ may be modified by a ratio equal to the ratio $CD_{DIFF}/CD_{OP}$. After modifying the selected threshold variable $h_1$, $\gamma$, or $\alpha$, the SEM image is again binarized (step 1940) using the adjusted threshold variable, $CD_{DIFF}$ is again produced through the above-described process (steps 1945, 1950, and 1953).

However, in step 1965, if the magnitude of $CD_{DIFF}$ is determined to be less than the small predefined constant $\delta$ (branch 1960), then the threshold variable indexed by the profile type is sufficiently accurate, and another grating can be obtained and the above described process (steps 1915, 1925, 1930, 1935, 1940, 1945, 1950, 1955, 1970 and 1975 or 1960 and 1965) repeated to further update and fine-tune the binarization table 1990 of FIG. 7B.

4. Use of CD-SEM Data for Optical Profilometry Library Generation

In one exemplary embodiment, CD-SEM can also be used to calibrate OP by providing an estimated critical dimension for a structure. The OP library generation process can then calculate diffraction spectra corresponding to a set of profile shapes with critical dimensions of roughly the critical dimension estimated by the CD-SEM. By this process, a reduced number of profiles and spectra can be generated to provide an adequate library.

FIG. 9 depicts an exemplary process to build a profile/spectrum library from initial data provided by CD-SEM. In step 2215, a diffraction grating is formed on a wafer. In step 2220, a CD-SEM is performed to obtain a CD-SEM critical dimension measurement, $CD_{SEM}$. In step 2225, profiles are generated based roughly on the measured line width $CD_{SEM}$. In step 2227, OP spectra corresponding to the OP profiles based roughly on the measured line width $CD_{SEM}$ are generated. In step 2230, OP spectral data is acquired from the grating. In step 2235, a best match is then found between the acquired spectrum and spectra in the library to estimate the profile of the grating lines.

5. Extension of Critical Dimension-Dependent Data via Optical Profilometry

In another exemplary embodiment, projection metrology data and studies, such as the critical dimension versus line width curve, can be extended to increasingly smaller dimensions using optical profilometry. The relation between transistor switching speed and critical dimension is shown in the graph 500 of FIG. 5. Region 510 on the left half of the graph 500 utilizes data points 505 and 507 acquired by CD-SEM measurements of existing transistor technologies, while region 520 on the right half of the graph 500 is a hypothetical extension of the data to future transistor technologies. However, due to the limitations of CD-SEM metrology discussed above, utilization of CD-SEM metrology for critical dimensions in region 520 will be increasingly more difficult.

FIG. 10 depicts an exemplary process to generate switching speed versus critical dimension data in the right-hand region 520 of the graph 500 of FIG. 5. In step 2105, a wafer is produced that has a diffraction grating and adjacent switching circuitry with the same critical dimension as the diffraction grating. In step 2123, an OP profile of the lines of the grating is then acquired, and an OP critical dimension, $CD_{OP}$, is extracted from the grating profile. In step 2127, a measurement is then made of the switching speed of the adjacent switching circuitry. In step 2135, an additional point (not depicted) is plotted on the graph 500 of FIG. 5 of critical dimension versus switching speed. In step 2155, if the additional point is determined not to lie in the known region 510 of the curve 530 of FIG. 5 (branch 2153), then the additional point 550 of FIG. 5 is saved. If the additional point is determined to lie in the known region 510 of the curve 530 of FIG. 5 (branch 2142), then this will confirm the accuracy of the OP critical dimension $CD_{OP}$ extraction method. Additionally, in step 2146, the line width of the diffraction grating can be reduced, and a new point plotted by performing the previously described steps 2105, 2120, 2123, 2125, 2127, 2135. Typically, the process of generating data for the graph 500 of FIG. 5 will begin with critical dimensions in the known region 510 of FIG. 5, so that the $CD_{OP}$ extraction process can be verified before generating points in the unknown region 520 of FIG. 5.

The foregoing descriptions of specific exemplary embodiments have been presented for purposes of illustration and description. They are not intended to be exhaustive or to limit the invention to the precise forms disclosed, and it should be understood that many modifications and variations are possible. For example, a wafer metrology system may have multiple on-loading docks and/or multiple off-loading docks; the transport device or conveyor may be a conveyor belt, a mechanical arm, or any other type of conveyor mechanism; the conveyor may hold more or fewer wafers than depicted in the figures; the scatterometer may be located near or on the off-loading dock rather than the on-loading dock; the loading docks, intermediate-vacuum chamber and high-vacuum chamber may have a geometry other than that depicted in the figures; the scatterometer may be mounted outside the CD-SEM system; a diffraction spectra acquisition system may utilize multiple detectors and multiple excitation heads; etc.

Furthermore, with regards to the wafer fabrication process for wafers: the fabrication process may differ from that described, and may include processes not described above; CD-SEM metrology and/or OP/CD-SEM metrology may be used during any stage of the fabrication process; each wafer may have multiple diffraction gratings, and metrology of multiple gratings on a single wafer may be used to provide information regarding spatial deviations; the path and motions of the wafers through the above-described apparatuses may be other than described; metrology may be performed on some or all of the wafers on the fabrication line; diffraction gratings may have more than 30 lines or less than 30 lines. The concepts and principles of the present embodiment can apply to optical metrology systems capable of measuring an IC structure having one line.

Furthermore, other binarizations methods and functions may be utilized; profiles may be classified based on a different set of profile types; physical properties other than specific gravity, dielectric constant, conductivity, and doping may be used to provide corrections to physical property errors; the physical property errors database and/or the loading effect database may not have an inactive status option; table, formula, fuzzy logic calculations, or neural net calculations may be used for any of the calculations or algorithms described; the databases and tables may take other forms, such as matrices or tensors; row and column indices may be swapped or reversed; other steps or alternative sequences of steps may be used to build the profile/spectrum library from CD-SEM provided initial data; other steps or alternative sequences of steps may be used to generate speed versus critical dimension graph points; other steps or alternative sequences of steps may be used for any of the processes or methods described; steps may be deleted from the processes or methods described; although the loading error correction and the physical properties error corrections are described as being used to correct errors in the critical dimension, a loading error correction may be applied to the CD-SEM image to provide a loading-corrected CD-SEM image, and/or a physical properties error correction may be applied to the CD-SEM image to provide a physical properties-corrected CD-SEM image; a technique other than rigorous coupled wave analysis may be used to calculate spectra corresponding to profiles, etc.

We claim:

1. A method for calibrating imaging data from microscopy of first structures using a first profile shape of the first structures determined from optical profilometry of the first structures, comprising:
   acquiring a first microscopy image of at least a first portion of the first structures;
   determining a first critical dimension estimate of the first structures from the first microscopy image;
   acquiring optical profilometry data of at least a second portion of the first structures;
   determining a second critical dimension estimate of the first structures from the profile shape; and
   determining a difference between the first critical dimension estimate and the second critical dimension estimate, the difference being dependent on at least one physical property of the first structures.

2. The method of claim 1 wherein the optical profilometry is performed by comparing a measured diffraction spectrum obtained from a scatterometer with calculated diffraction spectra from a library to find a best-match calculated spectrum which most closely matches the measured diffraction spectrum, whereby the first profile shape corresponding to the best-match calculated spectrum is an estimate of the physical profile of the first structures.

3. The method of claim 1 further including the step of correlating the difference between the first critical dimension estimate and the second critical dimension estimate with the at least one physical property.

4. The method of claim 3 wherein the at least one physical property includes dielectric constant, specific gravity, and/or conductivity.

5. The method of claim 3 further including the steps of:
   acquiring a second microscopy image of at least a portion of second structures;
   determining a third critical dimension estimate of the second structures from the second microscopy image; and
   correcting for the difference of the third critical dimension estimate based on the at least one physical property of the second structures to provide a corrected critical dimension estimate for the second structures.

6. The method of claim 5 wherein the first microscopy image is a first scanning electron microscope image and the second microscopy image is a second scanning electron microscope image.

7. The method of claim 1 wherein the first microscopy image is a first scanning electron microscope image.

8. A method for calibrating imaging data from a projection microscope using shape profiles determined from optical profilometry, comprising the steps of:
   acquiring a first microscopy image of at least a first portion of first structures;
   acquiring a second microscopy image of at least a second portion of second structures;
   determining a first critical dimension estimate of the first structures from the first microscopy image;
   determining a second critical dimension estimate of the second structures from the second microscopy image;
   acquiring first optical profilometry data of at least a third portion of the first structures to generate a first profile shape;
   acquiring second optical profilometry data of at least a fourth portion of the second structures to generate a second profile shape;
   determining a third critical dimension estimate of the first structures from the first profile shape;

determining a fourth critical dimension estimate of the second structures from the second profile shape; and determining differences between the first critical dimension estimate and the third critical dimension estimate and between the second critical dimension estimate and the fourth critical dimension estimate, the differences dependent on at least one physical property of the first structures and the second structures.

9. The method of claim 8 further including the step of:

correlating the difference between the first and third critical dimension estimates; and correlating the difference between the second and fourth critical dimension estimates with the at least one physical property.

10. A method for calibrating imaging data from microscopy of first structures using a first physical shape determined from optical profilometry of the first structures, comprising the steps of:

acquiring a first microscopy image of at least a first portion of the first structures;

determining a first critical dimension estimate of the first structures from the first microscopy image;

acquiring optical profilometry data of at least a second portion of the first structures to provide a profile shape;

determining a second critical dimension estimate of the first structures from the profile shape; and determining a difference dependent on a first density of the first structures between the first critical dimension estimate and the second critical dimension estimate.

11. The method of claim 10 wherein the first density of the first structures is determined from the optical profilometry data.

12. The method of claim 10 wherein the first density of the first structures is dependent on spacing between the first structures.

13. The method of claim 10 further including the steps of:

acquiring a second microscopy image of at least a third portion of second structures;

determining a third critical dimension estimate of the second structures from the second microscopy image;

determining a second density of the second structures; and correcting for the difference of the third critical dimension estimate based on the second density of the second structures to provide a corrected critical dimension estimate for the second structures.

14. The method of claim 13 wherein the second density of the second structures is determined from the second microscopy image.

15. The method of claim 13 wherein the first microscopy image is a first scanning electron microscope image and the second microscopy image is a second scanning electron microscope image.

16. The method of claim 10 wherein the first microscopy image is a first scanning electron microscope image.

17. A method for using microscopy to augment the use of optical profilometry to determine a profile shape of integrated circuit structures, comprising the steps of:

acquiring a microscopy image of at least a first portion of the integrated circuit structures;

determining a critical dimension estimate of the integrated circuit structures from the microscopy image; and generating a library of calculated diffraction spectra corresponding to a set of profile shapes with critical dimensions based on the critical dimension estimate obtained from the microscopy image.

18. The method of claim 17, further including the step of acquiring optical profilometry data of at least a second portion of the integrated circuit structures by comparing a measured diffraction spectrum with the calculated diffraction spectra in the library to find a best-match calculated spectrum which most closely matches the measured diffraction spectrum, whereby the profile shape corresponding to the best-match calculated spectrum is an estimate of the physical profile of the structures.

19. The method of claim 18 wherein the first portion of the integrated circuit structures is within the second portion of the integrated circuit structures.

20. The method of claim 17 wherein the microscopy image is a scanning electron microscope image.

21. A method for using optical profilometry to interpret microscopy imaging data, the method comprising the steps of:

acquiring a microscopy image of a first integrated circuit structure;

performing optical profilometry on second integrated circuit structures to determine a first profile shape;

classifying the first profile shape as a profile type selected from a set of profile types; and processing the microscopy image of the first integrated circuit structure based on the profile type.

22. The method of claim 21 wherein the performing optical profilometry includes comparing a measured diffraction spectrum with calculated diffraction spectra to find a best-match calculated spectrum which most closely matches the measured diffraction spectrum, whereby the first profile shape corresponding to the best-match calculated spectrum is an estimate of the physical profile of the second integrated circuit structures.

23. The method of claim 21 wherein the processing of the microscopy image step provides a determination of a first critical dimension estimate of the first integrated circuit structure.

24. The method of claim 23 wherein the first critical dimension estimate is dependent on intensity maximum and an intensity minimum of the microscopy image.

25. The method of claim 21 wherein the first integrated circuit structure and the second integrated circuit structures are fabricated according to the same process.

26. The method of claim 21 wherein the first integrated circuit structure and the second integrated circuit structures are fabricated on the same wafer.

27. The method of claim 21 wherein the first microscopy image is a first scanning electron microscope image.

28. A method for augmenting a function of critical dimension values versus a critical dimension dependent characteristic, critical dimension values of pre-augmented data of the function being based on microscopy of first integrated circuit structures, the function being augmented with augmentation data where critical dimension values are based on optical profilometry of second integrated circuit structures, the method comprising the steps of:

performing optical profilometry on a first portion of first structures to determine a first profile shape of the first structures;

determining a first critical dimension estimate corresponding to the first profile shape using optical profilometry;

determining a first critical dimension dependent characteristic corresponding to the first critical dimension estimate to provide a first critical dimension/critical dimension dependent characteristic data point; and adding the first critical dimension/critical dimension dependent characteristic data point to the pre-augmented data.

29. The method of claim 28 wherein the performing optical profilometry includes comparing a measured diffraction spectrum with calculated diffraction spectra to find a best-match calculated spectrum which most closely matches the measured diffraction spectrum, whereby the first profile shape corresponding to the best-match calculated spectrum is an estimate of the physical profile of the structures.

30. The method of claim 28 wherein the first integrated circuit structures include integrated circuit structures in common with the second integrated circuit structures.

31. The method of claim 28:

wherein the critical dimension values of the pre-augmented data of the function extend from a lower critical dimension value to an upper critical dimension value; and wherein the first critical dimension estimate is less than the lower critical dimension value.

32. The method of claim 28 wherein the function is a critical dimension versus switching speed curve.

33. The method of claim 28 further comprising the steps of:

acquiring a first microscopy image of at least a second portion of the first structures;

determining a second critical dimension estimate of the first structures from the first microscopy image; and correcting the first critical dimension/critical dimension dependent characteristic data point to correspond to the difference between the first critical dimension estimate and the second critical dimension estimate.

\* \* \* \* \*